United States Patent [19]

Strack et al.

[11] Patent Number: 5,336,552
[45] Date of Patent: Aug. 9, 1994

[54] NONWOVEN FABRIC MADE WITH MULTICOMPONENT POLYMERIC STRANDS INCLUDING A BLEND OF POLYOLEFIN AND ETHYLENE ALKYL ACRYLATE COPOLYMER

[75] Inventors: David C. Strack, Canton; Linda A. Connor, Atlanta; Sharon W. Gwaltney, Woodstock; Ann L. McCormack, Cumming; Susan E. Shawver; Jay S. Shultz, both of Roswell, all of Ga.

[73] Assignee: Kimberly-Clark Corporation, Neenah, Wis.

[21] Appl. No.: 936,142

[22] Filed: Aug. 26, 1992

[51] Int. Cl.$^5$ .......... B32B 5/26; B32B 27/02; D01F 8/06; D04H 3/14
[52] U.S. Cl. .......... 428/224; 264/DIG. 26; 428/286; 428/296; 428/373; 428/374
[58] Field of Search .......... 2/243 A; 428/224, 286, 428/296, 374, 373

[56] References Cited

U.S. PATENT DOCUMENTS

| Re. 30,955 | 6/1982 | Stanistreet | 156/308.2 |
| Re. 31,825 | 2/1985 | Mason et al. | 428/198 |
| 2,931,091 | 4/1960 | Breen | 28/82 |
| 2,987,797 | 6/1961 | Breen | 28/82 |

(List continued on next page.)

FOREIGN PATENT DOCUMENTS

| 612156 | 1/1961 | Canada . |
| 769644 | 10/1967 | Canada . |
| 792651 | 8/1968 | Canada . |
| 829845 | 12/1969 | Canada . |
| 846761 | 7/1970 | Canada . |
| 847771 | 7/1970 | Canada . |
| 852100 | 9/1970 | Canada . |
| 854076 | 10/1970 | Canada . |
| 959221 | 12/1974 | Canada . |
| 959225 | 12/1974 | Canada . |
| 989720 | 5/1976 | Canada . |
| 1172814 | 8/1984 | Canada . |
| 2001091 | 4/1990 | Canada . |
| 2011599 | 9/1990 | Canada . |
| 1286464 | 7/1991 | Canada . |
| 2067398 | 2/1992 | Canada . |
| 0013127 | 7/1980 | European Pat. Off. . |
| 0029666 | 6/1981 | European Pat. Off. . |
| 0070163 | 1/1983 | European Pat. Off. . |
| 0070164 | 1/1983 | European Pat. Off. . |
| 0078869 | 5/1983 | European Pat. Off. . |
| 0127483 | 12/1984 | European Pat. Off. . |
| 0132110 | 1/1985 | European Pat. Off. . |
| 0134141 | 3/1985 | European Pat. Off. . |
| 0171806 | 2/1986 | European Pat. Off. . |
| 0171807 | 2/1986 | European Pat. Off. . |
| 0233767 | 4/1988 | European Pat. Off. . |
| 0264112 | 4/1988 | European Pat. Off. . |
| 0275047 | 11/1988 | European Pat. Off. . |
| 0290945 | 11/1988 | European Pat. Off. . |
| 0334579 | 9/1989 | European Pat. Off. . |
| 0337296 | 10/1989 | European Pat. Off. . |
| 0370835 | 5/1990 | European Pat. Off. . |
| 077039 | 3/1990 | Japan . |

OTHER PUBLICATIONS

"Thermobonding Fibers for Nonwovens", By S. Tomioka, Nonwovens Industry, May 1981, pp. 23–24, 30–31.
"It's Time To Get To Know N–Butyl Acrylate Copolymers", B. Henn, Plastic Technology, Jun. 1992, pp. 71–74.
"Enathene TM Ethylene n–Butyl Acrylate Copolymers For Film and Extrusion Coating Technical & Comp. Data", Quantum Chem. Co. 1990.

Primary Examiner—James C. Cannon
Attorney, Agent, or Firm—William D. Herrick; Michael U. Lee

[57] ABSTRACT

A nonwoven fabric made with multicomponent polymeric strands includes a blend of a polyolefin and ethylene alkyl acrylate in one side or the sheath of the multicomponent polymeric strands. The fabric has improved abrasion resistance, strength, toughness and softness properties. Composite materials including such multicomponent material bonded to both sides of an inner meltblown layer are also disclosed.

75 Claims, 3 Drawing Sheets

U.S. PATENT DOCUMENTS

| | | | |
|---|---|---|---|
| 3,038,235 | 6/1962 | Zimmerman | 28/82 |
| 3,038,236 | 6/1962 | Breen | 28/82 |
| 3,038,237 | 6/1962 | Taylor, Jr. | 28/82 |
| 3,377,232 | 4/1968 | Meacock et al. | |
| 3,423,266 | 1/1969 | Davies et al. | 156/167 |
| 3,551,271 | 12/1970 | Thomas et al. | 161/150 |
| 3,589,956 | 6/1971 | Kranz et al. | 156/62.4 |
| 3,595,731 | 7/1971 | Davies et al. | |
| 3,616,160 | 10/1971 | Wincklhofer | |
| 3,692,618 | 9/1972 | Dorschner et al. | |
| 3,725,192 | 4/1973 | Ando et al. | |
| 3,760,046 | 9/1973 | Schwartz et al. | 264/47 |
| 3,802,817 | 4/1974 | Matsuki et al. | 425/66 |
| 3,824,146 | 7/1974 | Ellis | |
| 3,855,045 | 12/1974 | Brock | |
| 3,895,151 | 7/1975 | Matthews et al. | 428/102 |
| 3,900,678 | 8/1975 | Aishima et al. | 428/374 |
| 3,940,302 | 2/1976 | Matthews et al. | 156/167 |
| 3,992,499 | 11/1976 | Lee | 264/78 |
| 4,005,169 | 1/1977 | Cumbers | 264/103 |
| 4,068,036 | 1/1978 | Stanistreet | 428/296 |
| 4,076,698 | 2/1978 | Anderson et al. | 526/348.6 |
| 4,086,112 | 4/1978 | Porter | 156/73.1 |
| 4,088,726 | 5/1978 | Cumbers | 264/123 |
| 4,119,447 | 10/1978 | Ellis et al. | 156/73.1 |
| 4,154,357 | 5/1979 | Sheard et al. | 220/88 A |
| 4,170,680 | 10/1979 | Cumbers | 428/195 |
| 4,181,762 | 1/1980 | Benedyk | 428/97 |
| 4,188,436 | 2/1980 | Ellis et al. | 428/198 |
| 4,189,338 | 2/1980 | Ejima et al. | 156/167 |
| 4,195,112 | 3/1980 | Sheard et al. | 428/288 |
| 4,211,816 | 7/1980 | Booker et al. | 428/296 |
| 4,211,819 | 7/1980 | Kunimune et al. | 428/374 |
| 4,216,772 | 8/1980 | Tsuchiya et al. | 128/284 |
| 4,234,655 | 11/1980 | Kunimune et al. | 428/374 |
| 4,258,097 | 3/1981 | Benedyk | 428/224 |
| 4,269,888 | 5/1981 | Ejima et al. | 428/296 |
| 4,285,748 | 8/1981 | Booker et al. | 156/167 |
| 4,306,929 | 12/1981 | Menikheim et al. | 156/290 |
| 4,315,881 | 2/1982 | Nakajima et al. | 264/171 |
| 4,323,626 | 4/1982 | Kunimune et al. | 428/374 |
| 4,340,563 | 7/1982 | Appel et al. | 264/518 |
| 4,356,220 | 10/1982 | Benedyk | 428/17 |
| 4,362,777 | 12/1982 | Miller | 428/224 |
| 4,369,156 | 1/1983 | Mathes et al. | 264/147 |
| 4,373,000 | 2/1983 | Knoke et al. | 428/198 |
| 4,381,326 | 4/1983 | Kelly | 428/134 |
| 4,396,452 | 8/1983 | Menikheim et al. | 156/290 |
| 4,419,160 | 12/1983 | Wang et al. | 156/73.2 |
| 4,434,204 | 2/1984 | Hartman et al. | 428/198 |
| 4,451,520 | 5/1984 | Tecl et al. | 428/198 |
| 4,469,540 | 9/1984 | Furukawa et al. | 156/62.4 |
| 4,477,516 | 10/1984 | Sugihara et al. | 428/296 |
| 4,480,000 | 10/1984 | Watanabe et al. | 428/284 |
| 4,483,897 | 11/1984 | Fujimura et al. | 428/288 |
| 4,485,141 | 11/1984 | Fujimura et al. | 428/288 |
| 4,496,508 | 1/1985 | Hartmann et al. | 264/167 |
| 4,500,384 | 2/1985 | Tomioka et al. | 156/290 |
| 4,504,539 | 3/1985 | Petracek et al. | 428/195 |
| 4,511,615 | 4/1985 | Ohta | 428/198 |
| 4,520,066 | 5/1985 | Athey | 428/288 |
| 4,530,353 | 7/1985 | Lauritzen | 128/156 |
| 4,546,040 | 10/1985 | Knotek et al. | 428/370 |
| 4,547,420 | 10/1985 | Krueger et al. | 428/229 |
| 4,551,378 | 11/1985 | Carey, Jr. | 428/198 |
| 4,552,603 | 11/1985 | Harris, Jr. et al. | 156/167 |
| 4,555,430 | 11/1985 | Mays | 428/134 |
| 4,555,811 | 12/1985 | Shimalla | 2/81 |
| 4,557,972 | 12/1985 | Okamoto et al. | 428/373 |
| 4,588,630 | 5/1986 | Shimalla | 428/131 |
| 4,595,629 | 6/1986 | Mays | 428/286 |

(List continued on next page.)

U.S. PATENT DOCUMENTS

| | | | |
|---|---|---|---|
| 4,632,858 | 12/1986 | Knoke et al. | 428/287 |
| 4,644,045 | 2/1987 | Fowells | 526/348 |
| 4,656,075 | 4/1987 | Mudge | 428/110 |
| 4,657,804 | 4/1987 | Mays et al. | 428/212 |
| 4,663,220 | 5/1987 | Wisneski et al. | 428/221 |
| 4,681,801 | 7/1987 | Eian et al. | 428/283 |
| 4,684,570 | 8/1987 | Malaney | 428/296 |
| 4,713,134 | 12/1987 | Mays et al. | 156/181 |
| 4,713,291 | 12/1987 | Sasaki et al. | 428/373 |
| 4,722,857 | 2/1988 | Tomioka et al. | 428/113 |
| 4,731,277 | 3/1988 | Groitzsch et al. | 428/137 |
| 4,737,404 | 4/1988 | Jackson | 428/284 |
| 4,749,423 | 6/1988 | Vaalburg et al. | 156/181 |
| 4,755,179 | 7/1988 | Shiba et al. | 604/370 |
| 4,756,786 | 7/1988 | Malaney | 156/308.2 |
| 4,770,925 | 9/1988 | Uchikawa et al. | 428/219 |
| 4,774,124 | 9/1988 | Shimalla et al. | 428/171 |
| 4,774,277 | 9/1988 | Janac et al. | 524/474 |
| 4,787,947 | 11/1988 | Mays | 156/160 |
| 4,789,699 | 12/1988 | Kieffer et al. | 524/271 |
| 4,795,559 | 1/1989 | Shinjou et al. | 210/490 |
| 4,795,668 | 1/1989 | Krueger et al. | 428/174 |
| 4,804,577 | 2/1989 | Hazelton et al. | 428/224 |
| 4,808,202 | 2/1989 | Nishikawa et al. | 55/390 |
| 4,814,032 | 3/1989 | Taniguchi et al. | 156/167 |
| 4,818,587 | 4/1989 | Ejima et al. | 428/198 |
| 4,830,904 | 5/1989 | Gessner et al. | 428/219 |
| 4,839,228 | 6/1989 | Jezic et al. | 428/401 |
| 4,840,846 | 6/1989 | Ejima et al. | 428/373 |
| 4,840,847 | 6/1989 | Ohmae et al. | 428/373 |
| 4,851,284 | 7/1989 | Yamanoi et al. | 428/284 |
| 4,872,870 | 10/1989 | Jackson | 504/366 |
| 4,874,447 | 10/1989 | Hazelton et al. | 156/167 |
| 4,874,666 | 10/1989 | Kubo et al. | 428/398 |
| 4,880,691 | 11/1989 | Sawyer et al. | 428/225 |
| 4,883,707 | 11/1989 | Newkirk | 428/219 |
| 4,909,975 | 3/1990 | Sawyer et al. | 264/210.7 |
| 4,966,808 | 10/1990 | Kawano | 428/224 |
| 4,981,749 | 1/1991 | Kubo et al. | 428/219 |
| 4,997,611 | 3/1991 | Hartmann | 264/210.8 |
| 5,001,813 | 3/1991 | Rodini | 19/0.46 |
| 5,002,815 | 3/1991 | Yamanaka et al. | 428/109 |
| 5,059,482 | 10/1991 | Kawamoto et al. | 428/373 |
| 5,068,141 | 11/1991 | Kubo et al. | 428/219 |
| 5,069,970 | 12/1991 | Largman et al. | 428/373 |
| 5,082,720 | 1/1992 | Hayes | 428/373 |
| 5,108,276 | 4/1992 | Hartmann | 425/66 |
| 5,108,820 | 4/1992 | Kaneko et al. | 428/198 |
| 5,108,827 | 4/1992 | Gessner | 428/219 |
| 5,125,818 | 6/1992 | Yeh | 425/131.5 |
| 5,126,201 | 6/1992 | Shiba et al. | 428/389 |
| 5,130,196 | 7/1992 | Nishio | 428/373 |
| 5,133,917 | 7/1992 | Jezic et al. | 428/373 |

NONWOVEN FABRIC MADE WITH MULTICOMPONENT POLYMERIC STRANDS INCLUDING A BLEND OF POLYOLEFIN AND ETHYLENE ALKYL ACRYLATE COPOLYMER

TECHNICAL INFORMATION

This invention generally relates to polymeric fabrics, and more particularly relates to multicomponent nonwoven polymeric fabrics.

BACKGROUND OF THE INVENTION

Nonwoven fabrics are used to make a variety of products, which desirably have particular levels of softness, strength, durability, uniformity, liquid handling properties such as absorbency, liquid barrier properties and other physical properties. Such products include towels, industrial wipes, incontinence products, infant care products such as baby diapers, absorbent feminine care products, and garments such as medical apparel. These products are often made with multiple layers of nonwoven fabric to obtain the desired combination of properties. For example, disposable baby diapers made from nonwoven fabrics may include a liner layer which fits next to the baby's skin and is soft, strong and porous, an impervious outer cover layer which is strong and soft, and one or more interior liquid handling layers which are soft and absorbent.

Nonwoven fabrics such as the foregoing are commonly made by melt spinning thermoplastic materials. Such fabrics are called spunbond materials and methods for making spunbond polymeric materials are well-known. U.S. Pat. No. 4,692,618 to Dorschner et al. and U.S. Pat. No. 4,340,563 to Appel et al. both disclose methods for making spunbond nonwoven webs from thermoplastic materials by extruding the thermoplastic material through a spinneret and drawing the extruded material into filaments with a stream of high velocity air to form a random web on a collecting surface. For example, U.S. Pat. No. 3,692,618 to Dorschner et al. discloses a process wherein bundles of polymeric filaments are drawn with a plurality of eductive guns by very high speed air. U.S. Pat. No. 4,340,563 to Appel et al. discloses a process wherein thermoplastic filaments are drawn through a single wide nozzle by a stream of high velocity air. The following patents also disclose typical melt spinning processes: U.S. Pat. No. 3,338,992 to Kinney; U.S. Pat. No. 3,341,394 to Kinney; U.S. Pat. No. 3,502,538 to Levy; U.S. Pat. No. 3,502,763 to Hartmann; U.S. Pat. No. 3,909,009 to Hartmann; U.S. Pat. No. 3,542,615 to Dobo et al.; and Canadian Patent Number 803,714 to Harmon.

Spunbond materials with desirable combinations of physical properties, especially combinations of softness, strength and durability, have been produced, but limitations have been encountered. For example, for some applications, polymeric materials such as polypropylene may have a desirable level of strength but not a desirable level of softness. On the other hand, materials such as polyethylene may, in some cases, have a desirable level of softness but not a desirable level of strength.

In an effort to produce nonwoven materials having desirable combinations of physical properties, multicomponent or bicomponent nonwoven fabrics have been developed. Methods for making bicomponent nonwoven materials are well-known and are disclosed in patents such as Reissue Number 30,955 of U.S. Pat. No. 4,068,036 to Stanistreet, U.S. Pat. No. 3,423,266 to Davies et al., and U.S. Pat. No. 3,595,731 to Davies et al. A bicomponent nonwoven fabric is made from polymeric fibers or filaments including first and second polymeric components which remain distinct. As used herein, filaments mean continuous strands of material and fibers mean cut or discontinuous strands having a definite length. The first and second components of multicomponent filaments are arranged in substantially distinct zones across the cross-section of the filaments and extend continuously along the length of the filaments. Typically, one component exhibits different properties than the other so that the filaments exhibit properties of the two components. For example, one component may be polypropylene which is relatively strong and the other component may be polyethylene which is relatively soft. The end result is a strong yet soft nonwoven fabric.

U.S. Pat. No. 3,423,266 to Davies et al. and U.S. Pat. No. 3,595,731 to Davies et al. disclose methods for melt spinning bicomponent filaments to form nonwoven polymeric fabrics. The nonwoven webs may be formed by cutting the meltspun filaments into staple fibers and then forming a bonded carded web or by laying the continuous bicomponent filaments onto a forming surface and thereafter bonding the web.

To increase the bulk of the bicomponent nonwoven webs, the bicomponent fibers or filaments are often crimped. As disclosed in U.S. Pat. Nos. 3,595,731 and 3,423,266 to Davies et al., bicomponent filaments may be mechanically crimped and the resultant fibers formed into a nonwoven web or, if the appropriate polymers are used, a latent helical crimp, produced in bicomponent fibers or filaments may be activated by heat treatment of the formed web. The heat treatment is used to activate the helical crimp in the fibers or filaments after the fibers or filaments have been formed into a nonwoven web.

Particularly for outer cover materials such as the outer cover layer of a disposable baby diaper, it is desirable to improve the durability and softness of nonwoven polymeric fabric. The durability of nonwoven polymeric fabric can be improved by increasing the abrasion resistance of the fabric. The abrasion resistance may be increased by increasing the give of the fabric. For example, with multicomponent nonwoven bonds between the multicomponent fabrics including a softer component such as polyethylene and a high strength component such as polypropylene, the strands tend to pull apart when subjected to a sufficient load. To produce a more durable fabric, it is desirable to increase the durability of the bonds between such multicomponent polymeric strands and between the multicomponent fabric and other sheets of polymeric materials to which the multicomponent fabric may be laminated.

Therefore, there is a need for a nonwoven polymeric fabric which has enhanced levels of softness and durability, particularly for uses such as an outer cover material for absorbent personal care articles and garment material.

SUMMARY OF THE INVENTION

Accordingly, an object of the present invention is to provide improved nonwoven fabrics and methods for making the same.

Another object of the present invention is to provide nonwoven fabrics with desirable combinations of physical properties such as softness, strength, durability, uniformity and absorbency and methods for making the same.

A further object of the present invention is to provide a soft yet durable nonwoven outer cover material for absorbent personal care products such as disposable baby diapers.

Another object of the present invention is to provide a soft, yet durable, nonwoven garment material for items such as medical apparel.

Thus, the present invention provides a nonwoven fabric comprising multicomponent polymeric strands wherein one component includes a blend of a polyolefin and an ethylene alkyl acrylate copolymer. The ethylene alkyl acrylate copolymer provides more durable bonds between strands of the fabric and thereby enhances the abrasion resistance of the fabric. More specifically, the ethylene alkyl acrylate copolymer increases the give of the strands of the fabric at their bond points so that the fabric has more give and a higher abrasion resistance. At the same time, the ethylene alkyl acrylate copolymer increases other strength properties of the fabric and improves the softness, drape and conformability of the fabric. Furthermore, the addition of ethylene alkyl acrylate copolymer enhances the natural helical crimp of the multicomponent strands which increases the bulk of the fabric. The addition of ethylene alkyl acrylate copolymer allows the strands to be highly crimped at lower temperatures as will be explained in more detail below. When properly bonded, the nonwoven fabric of the present invention is particularly suited for use as an outer cover material in absorbent personal care products such as disposable baby diapers and as a garment material to make items such as medical apparel. For use as an outer cover or garment material, the fabric of the present invention may be laminated to a polymeric film, such as a polyethylene film, which can function as a liquid barrier.

More particularly, the nonwoven fabric of the present invention comprises extruded multicomponent polymeric strands including first and second polymeric components arranged in substantially distinctive zones across the cross-section of the multicomponent strands and extending continuously along the length of the multicomponent strands. Preferably the strands are continuous filaments which may be formed by spunbonding techniques. The second component of the strands constitutes at least a portion of the peripheral surface of the multicomponent strands continuously along the length of the multicomponent strands and includes a blend of a polyolefin and an ethylene alkyl acrylate copolymer. Bonds between the multicomponent strands may be formed by the application of heat. As explained above, the addition of the ethylene alkyl acrylate copolymer enhances the durability of the bonds between the multicomponent strands.

Still more specifically, the first polymeric component of the multicomponent strands of the present invention is present in an amount of from about 20 to about 80% by weight of the strands and the second polymeric component is present in an amount from about 80 to about 20% by weight of the strands. Preferably, the first polymeric component of the multicomponent strands of the present invention is present in an amount of from about 40 to about 60% by weight of the strands and the second polymeric component is present in an amount from about 60 to about 40% by weight of the strands. In addition, the ethylene alkyl acrylate copolymer is preferably present in an amount of from about 2 to about 50% by weight of the second component and the polyolefin is present in the second component in an amount of from about 98 to about 50% by weight of the second component. More preferably, the ethylene alkyl acrylate copolymer is present in an amount of from about 5 to about 25% by weight of the second component and the polyolefin is present in the second component in an amount of from about 95 to about 75% by weight of the second component. Still more preferably, the ethylene alkyl acrylate copolymer is present in an amount of from about 10 to about 20% by weight of the second component and the polyolefin is present in the second component in an amount of from about 90 to about 80% by weight of the second component.

Suitable ethylene acrylate copolymers include ethylene butyl acrylate, ethylene ethyl acrylate, and ethylene methyl acrylate copolmers. Ethylene n-butyl acrylate is a preferred copolymer.

According to another aspect of the present invention, a composite nonwoven fabric is provided. The composite fabric of the present invention includes a first web of extruded multicomponent polymeric strands such as is described above including multicomponent polymeric strands with a blend of a polyolefin and an ethylene alkyl acrylate copolymer in the second component of the multicomponent strands. The composite fabric of the present invention further comprises a second web of extruded polymeric strands, the first and second webs being positioned in laminar surface-to-surface relationship and bonded together to form an integrated fabric. The addition of the ethylene alkyl acrylate copolymer to the second component of the multicomponent strands of the first web enhances the durability of the bond between the first web and the second web. This improves the abrasion resistance and give of the overall composite.

More particularly, the strands of the second web of the composite of the present invention may be formed by conventional meltblowing techniques. Even more particularly, the strands of the second web preferably include a second blend of a polyolefin and an ethylene alkyl acrylate copolymer. The presence of ethylene alkyl acrylate copolymer in the first web and the second web enhances the bond between the webs and the overall durability of the composite.

Still more particularly, the composite fabric of the present invention preferably further comprises a third web of extruded multicomponent polymeric strands including first and second polymeric components arranged as in the first web, the second component including a third blend of a polyolefin and ethylene alkyl acrylate copolymer. The first web is bonded to one side of the second web and the third web is bonded to the opposite side of the second web. The presence of the ethylene alkyl acrylate copolymer enhances the durability of the bonds between the three webs and the overall durability of the composite fabric.

Preferably, in the multilayer fabric of the present invention, the strands of the first and third webs are continuous filaments which may be formed by spunbonding techniques and the strands of the second or middle web may be formed by meltblowing techniques. The composite fabric of the present invention is a cloth-like material particularly suited for use as a garment material or an outer cover material for personal care absorbent articles.

Still further objects and the broad scope of applicability of the present invention will become apparent to those of skill in the art from the details given hereinafter. However, it should be understood that the detailed description of the preferred embodiments of the present invention is given only by way of illustration because various changes and modifications well within the spirit and scope of the invention should become apparent to those of skill in the art in view of the following detailed description.

DETAILED DESCRIPTION OF THE INVENTION

Figure 1:
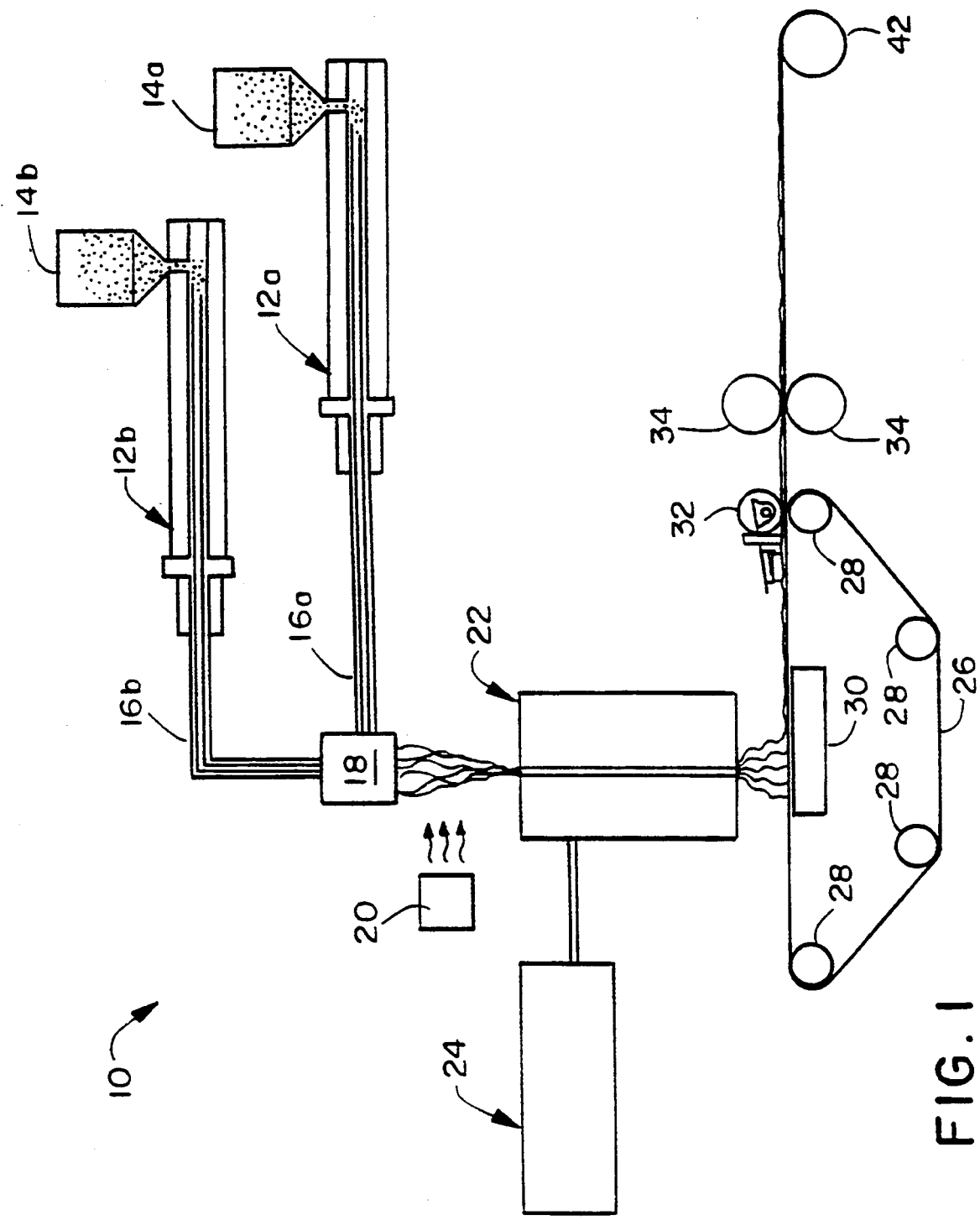
FIG. 1 is a schematic drawing of a process line for making a preferred embodiment of the present invention.

As discussed above, the present invention provides a soft, yet durable, cloth-like nonwoven fabric made with multicomponent polymeric strands. The nonwoven fabric of the present invention comprises extruded multicomponent strands including a blend of a polyolefin and an ethylene alkyl acrylate copolymer as one of the components. The ethylene alkyl acrylate copolymer imparts some give to the bond points between the multicomponent strands and thereby enables the fabric to better distribute stress. As a result, the fabric of the present invention has improved tensile elongation, tensile energy, abrasion resistance and softness. Furthermore, the ethylene alkyl acrylate copolymer enhances the natural helical crimp of the multicomponent strands and allows the strands to be highly crimped at lower temperatures.

The fabric of the present invention is particularly suited for making outer cover materials for personal care articles and garment materials. Suitable personal care articles include infant care products such as disposable baby diapers, child care products such as training pants, and adult care products such as incontinence products and feminine care products. Suitable garment materials include items such as medical apparel, work wear, and the like. For use as an outer cover or garment material, the fabric of the present invention may be laminated to a polymeric film, such as a polyethylene film, which can function as a liquid barrier. The ethylene alkyl acrylate enhances the durability of the bond between the nonwoven fabric and the polymeric film.

Suitable ethylene alkyl acrylate copolymers include ethylene butyl acrylate, ethylene ethyl acrylate, and ethylene methyl acrylate copolmers. Ethylene n-butyl acrylate is a preferred copolymer.

In addition, the present invention comprehends a nonwoven composite fabric including a first web of nonwoven fabric including multicomponent polymeric strands as described above and a second web of extruded polymeric strands bonded to the first web in laminar surface-to-surface relationship with the first web. According to a preferred embodiment of the present invention, such a composite material includes a third web of extruded multicomponent polymeric strands bonded to the opposite side of the second web to form a three layer composite. Each layer may include a blend of a polyolefin and ethylene alkyl acrylate copolymer for improved overall abrasion resistance of the composite.

The term strand as used herein refers to an elongated extrudate formed by passing a polymer through a forming orifice such as a die. Strands include fibers, which are discontinuous strands having a definite length, and filaments, which are continuous strands of material. The nonwoven fabric of the present invention may be formed from staple multicomponent fibers. Such staple fibers may be carded and bonded to form the nonwoven fabric. Preferably, however, the nonwoven fabric of the present invention is made with continuous spunbond multicomponent filaments which are extruded, drawn, and laid on a traveling forming surface. A preferred process for making the nonwoven fabrics of the present invention is disclosed in detail below.

As used herein, the terms "nonwoven web" and "nonwoven fabric" are used interchangeably to mean a web of material which has been formed without use of weaving processes which produce a structure of individual strands which are interwoven in an identifiable repeating manner. Nonwoven webs may be formed by a variety of processes such as meltblowing processes, spunbonding processes, film aperturing processes and staple fiber carding processes.

The fabric of the present invention includes extruded multicomponent polymeric strands comprising first and second polymeric components. The first and second components are arranged in substantially distinct zones across the cross-section of the multicomponent strands and extend continuously along the length of the multicomponent strands. The second component of the multicomponent strands constitutes a portion of the peripheral surface of the multicomponent strands continuously along the length of the multicomponent strands and includes a blend of a polyolefin and ethylene alkyl acrylate copolymer.

Figure 2A:
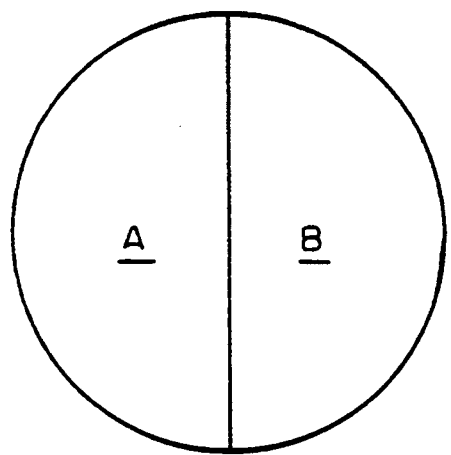
FIG. 2A is a schematic drawing illustrating the cross-section of a filament made according to a preferred embodiment of the present invention with the polymer components A and B in a side-by-side arrangement.
Figure 2B:
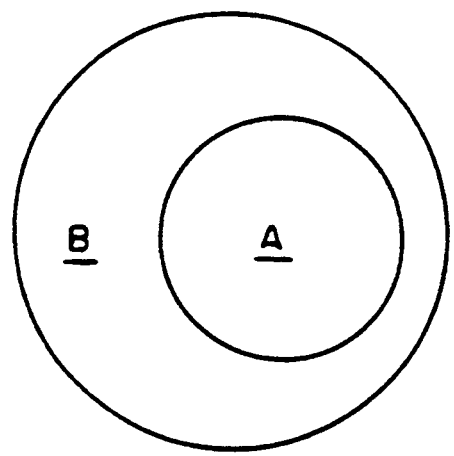
FIG. 2B is a schematic drawing illustrating the cross-section of a filament made according to a preferred embodiment of the present invention with the polymer components A and B in an eccentric sheath/core arrangement.
Figure 2C:
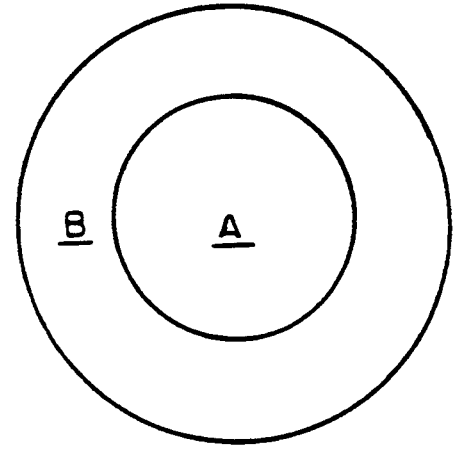
FIG. 2C is a schematic drawing illustrating the cross-section of a filament made according to a preferred embodiment of the present invention with the polymer components A and B in an concentric sheath/core arrangement.

A preferred embodiment of the present invention is a nonwoven polymeric fabric including bicomponent filaments comprising a first polymeric component A and a second polymeric component B. The first and second components A and B may be arranged in a side-by-side arrangement as shown in FIG. 2A or an eccentric sheath/core arrangement as shown in FIG. 2B so that the resulting filaments can exhibit a high level of natural helical crimp. Polymer component A is the core of the strand and polymer B is the sheath of the strand in the sheath/core arrangement. The first and second components may also be formed into a concentric sheath/core arrangement, as shown in FIG. 2C, or other multicomponent arrangements. Methods for extruding multicomponent polymeric strands into such arrangements are well known to those of ordinary skill in the art. Although the embodiments disclosed herein include bicomponent filaments, it should be understood that the fabric of the present invention may include strands having greater than 2 components.

The first component A of the multicomponent strands preferably has a melting point higher than the second component. More preferably, the first component A includes a polyolefin and the second component includes a blend of a polyolefin and a ethylene alkyl acrylate. Suitable polyolefins for the first component A include polypropylene, random copolymers of propylene and ethylene and poly(4-methyl-1-pentene); however, it should be understood that the first component A may also comprise other thermoplastic polymers such as polyesters or polyamides. Suitable polyolefins for the second component B include polyethylene and random copolymers of propylene and ethylene. Preferred polyethylenes for the the second component B includes linear low density polyethylene and high density polyethylene.

Preferred combinations of polymers for components A and B include (1) polypropylene as the first component A and a blend of linear low density polyethylene and ethylene n-butyl acrylate copolymer as the second component B, and (2) polypropylene as the first component A and a blend of random copolymer of ethylene and propylene and ethylene n-butyl acrylate copolymer as component B.

Suitable materials for preparing the multicomponent strands of the fabric of the present invention include PD-3445 polypropylene available from Exxon, Houston, Texas, a random copolymer of propylene and ethylene available from Exxon, ASPUN 6811A, 6808A and 6817 linear low density polyethylene available from Dow Chemical Company of Midland, Mich., and ENATHENE 720-009 ethylene n-butyl acrylate copolymer available from Quantum Chemical Corporation, USI Division of Cincinnati, Ohio.

While the principle components of the multicomponent strands of the present invention have been described above, such polymeric components can also include other materials which do not adversely effect the objectives of the present invention. For example, the polymeric components A and B can also include, without limitation, pigments, anti-oxidants, stabilizers, surfactants, waxes, flow promoters, solid solvents, particulates and materials added to enhance processability of the composition.

According to a preferred embodiment of the present invention, the multicomponent strands include from about 20 to about 80% by weight of the first polymeric component A and from about 80 to about 20% by weight of the second polymeric component B. The second component B preferably comprises from about 98 to about 50% by weight of a polyolefin and from about 2 to about 50% by weight of the ethylene alkyl acrylate copolymer. More preferably, the second component B comprises from about 95 to about 75% by weight of a polyolefin and from about 5 to about 25% by weight of the ethylene alkyl acrylate copolymer. Even more preferably, the second component B comprises from about 90 to about 80% by weight of a polyolefin and from about 10 to about 20% by weight of the ethylene alkyl acrylate copolymer.

According to one preferred embodiment of the present invention, a nonwoven fabric includes continuous spunbond bicomponent filaments comprising 50% by weight of a polymeric component A and 50% by weight of a polymeric component B in a side-by-side arrangement, polymeric component A comprising 100% by weight of polypropylene and the polymeric component B comprising 85% polyethylene and 15% ethylene n-butyl acrylate copolymer. In an alternative embodiment, the polyethylene in the second polymeric component B is substituted with random copolymer of ethylene and propylene.

Turning to FIG. 1, a process line 10 for preparing a preferred embodiment of the present invention is disclosed. The process line 10 is arranged to produce bicomponent continuous filaments, but it should be understood that the present invention comprehends nonwoven fabrics made with multicomponent filaments having more than two components. For example, the fabric of the present invention can be made with filaments having three or four components.

The process line 10 includes a pair of extruders 12a and 12b for separately extruding a polymer component A and a polymer component B. Polymer component A is fed into the respective extruder 12a from a first hopper 14a and polymer component B is fed into the respective extruder 12b from a second hopper 14b. Polymer components A and B are fed from the extruders 12a and 12b through respective polymer conduits 16a and 16b to a spinneret 18. Spinnerets for extruding bicomponent filaments are well-known to those of ordinary skill in the art and thus are not described here in detail. Generally described, the spinneret 18 includes a housing containing a spin pack which includes a plurality of plates stacked one on top of the other with a pattern of openings arranged to create flow paths for directing polymer components A and B separately through the spinneret. The spinneret 18 has openings arranged in one or more rows. The spinneret openings form a downwardly extending curtain of filaments when the polymers are extruded through the spinneret. Preferably, spinneret 18 is arranged to form side-by-side or eccentric sheath/core bicomponent filaments. Such configurations are shown in FIG. 2A and 2B respectively.

The process line 10 also includes a quench blower 20 positioned adjacent the curtain of filaments extending from the spinneret 18. Air from the quench air blower 20 quenches the filaments extending from the spinneret 18. The quench air can be directed from one side of the filament curtain as shown in FIG. 1, or both sides of the filament curtain.

A fiber draw unit or aspirator 22 is positioned below the spinneret 18 and receives the quenched filaments. Fiber draw units or aspirators for use in melt spinning polymers are well-known as discussed above. Suitable fiber draw units for use in the process of the present invention include a linear fiber aspirator of the type shown in U.S. Pat. No. 3,802,817 and eductive guns of the type shown in U.S. Pat. Nos. 3,692,618 and 3,423,266, the disclosures of which patents are hereby incorporated herein by reference.

Generally described, the fiber draw unit 22 includes an elongated vertical passage through which the filaments are drawn by aspirating air entering from the sides of the passage and flowing downwardly through the passage. The aspirating air draws the filaments and ambient air through the fiber draw unit. The aspirating air is heated by a heater 24 when a high degree of natural helical crimp in the filaments is desired.

An endless foraminous forming surface 26 is positioned below the fiber draw unit 22 and receives the continuous filaments from the outlet opening of the fiber draw unit. The forming surface 26 travels around guide rollers 28. A vacuum 30 positioned below the forming surface 26 where the filaments are deposited draws the filaments against the forming surface.

The process line 10 further includes a compression roller 32 which can be heated. The compression roller 32 along with the forward most of the guide rollers 28, receive the web as the web is drawn off of the forming surface 26. In addition, the process line includes a pair of thermal point bonding rollers 34 for bonding the bicomponent filaments together and integrating the web to form a finished fabric. Lastly, the process line 10 includes a winding roll 42 for taking up the finished fabric.

To operate the process line 10, the hopper 14a and 14b are filled with the respective polymer components A and B. Polymer components A and B are melted and extruded by the respected extruders 12a and 12b through polymer conduits 16a and 16b and the spinneret 18. Although the temperatures of the molten polymers vary depending on the polymers used, when polypropylene and polyethylene are used as components A and B respectively, the preferred temperatures of the polymers range from about 370° to about 530° F. and preferably range from 390° to about 450° F.

As the extruded filaments extend below the spinneret 18, a stream of air from the quench blower 20 at least partially quenches the filaments. The partial quenching may be used to develop a latent helical crimp in the filaments. The quench air preferably flows in a direction substantially perpendicular to the length of the filaments at a temperature of about 45° to about 90° F. and a velocity from about 100 to about 400 feet per minute.

After quenching, the filaments are drawn into the vertical passage of the fiber draw unit 22 by a flow of air through the fiber draw unit. The fiber draw unit is preferably positioned 30 to 60 inches below the bottom of the spinneret 18. When filaments having minimal natural helical crimp are desired, the aspirating air is at ambient temperature. When filaments having a high degree of crimp are desired, heated air from the heater 24 is supplied to the fiber draw unit 22. For high crimp, the temperature of the air supplied from the heater 24 is sufficient that, after some cooling due to mixing with cooler ambient air aspirated with the filaments, the air heats the filaments to a temperature requied to activate the latent crimp. The temperature required to activate the latent crimp of the filaments ranges from about 110° F. to a maximum temperature less than the melting point of the second component B. The temperature of the air from the heater 24 and thus the temperature to which the filaments are heated can be varied to achieve different levels of crimp. It should be further understood that the temperature of the air contacting the filaments to achieve the desired crimp will depend on factors such as the type of polymers in the filaments and the denier of the filaments.

Generally, a higher air temperature produces a higher number of crimps. The degree of crimp of the filaments may be controlled by controlling the temperature of the mixed air in the fiber draw unit 22 contacting the filaments. This allows one to change the resulting density, pore size distribution and drape of the fabric by simply adjusting the temperature of the air in the fiber draw unit.

Figure 3:
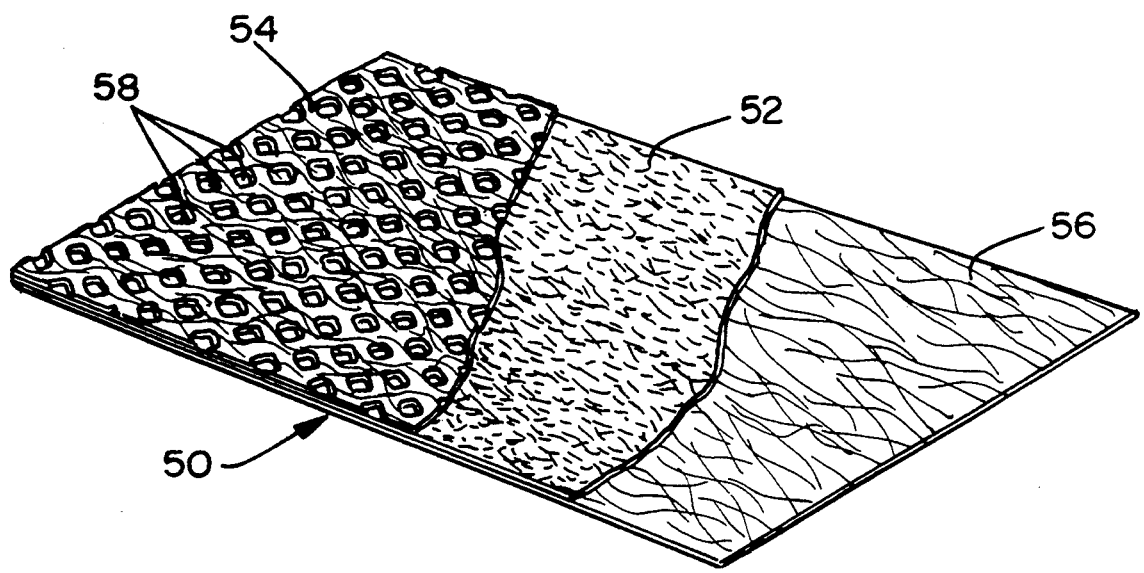
FIG. 3 is a fragmentary perspective view, with sections thereof broken away, of a point-bonded sample of multilayer fabric made according to a preferred embodiment of the present invention.

The drawn filaments are deposited through the outer opening of the fiber draw unit 22 onto the traveling forming surface 26. The vacuum 20 draws the filaments against the forming surface 26 to form an unbonded, nonwoven web of continuous filaments. The web is then lightly compressed by the compression roller 22 and thermal point bonded by bonding rollers 34. Thermal point bonding techniques are well known to those skilled in the art and are not discussed here in detail. Thermal point bonding in accordance with U.S. Pat. No. 3,855,046 is preferred and such reference is incorporated herein by reference. The type of bond pattern may vary based on the degree of strength desired. The bonding temperature also may vary depending on factors such as the polymers in the filaments but is preferably between about 240° and 255° F. As explained below, thermal point bonding is preferred when making cloth-like materials for such uses as the outer cover of absorbent personal care items like baby diapers and as garment materials for items like medical apparel. A thermal point bonded material is shown in FIG. 3.

Lastly, the finished web is wound onto the winding roller 42 and is ready for further treatment or use. When used to make liquid absorbent articles, the fabric of the present invention may be treated with conventional surface treatments or contain conventional polymer additives to enhance the wettability of the fabric. For example, the fabric of the present invention may be treated with polyalkaline-oxide modified siloxane and silanes such as polyalkaline-dioxide modified polydimethyl-siloxane as disclosed in U. S. Pat. No. 5,057,361. Such a surface treatment enhances the wettability of the fabric so that the nonwoven fabric is suitable as a liner or surge management material for feminine care, infant care, child care, and adult incontinence products. The fabric of the present invention may also be treated with other treatments such as antistatic agents, alcohol repellents, and the like, as known to those skilled in the art.

The resulting material is soft yet durable. The addition of the ethylene alkyl acrylate enhances the abrasion resistance and give of the fabric without diminishing the softness of the fabric. The ethylene alkyl acrylate copolymer imparts more give to the bond points between the multicomponent filaments enabling the fabric to better distribute stress.

When used as an outer cover material for personal care articles, the fabric of the present invention preferably has a denier from about 1 to about 12 dpf and more preferably has a denier from about 2 to about 3.5 dpf. The lower denier imparts improved cloth-like tactile properties to the fabric. The basis weight of such outer cover materials may vary but preferably ranges from about 0.4 to about 3.0 osy.

Although the method of bonding shown in FIG. 1 is thermal point bonding, it should be understood that the fabric of the present invention may be bonded by other means such as oven bonding, ultrasonic bonding, hydroentangling or combinations thereof to make cloth-like fabric. Such bonding techniques are well known to those of ordinary skill in the art and are not discussed here in detail. If a loftier material is desired, a fabric of the present invention may be bonded by non-compressive means such as through-air bonding. Methods of through-air bonding are well known to those of skill in the art. Generally described, the fabric of the present invention may be through-air bonded by forcing air having a temperature above the melting temperature of the second component B of the filaments through the fabric as the fabric passes over a perforated roller. The hot air melts the lower melting polymer component B and thereby forms bonds between the bicomponent filaments to integrate the web. Such a high loft material is useful as a fluid management layer of personal care absorbent articles such as liner or surge materials in a baby diaper.

According to another aspect of the present invention, the above described nonwoven fabric may be laminated to one or more polymeric layers to form a composite material. For example, an outer cover material may be formed by laminating the spunbond, nonwoven, thermal point bonded fabric described above to a polymeric film. The polymeric film can act as a liquid barrier and preferably comprises a polyolefin such as polypropylene or polyethylene and preferably has a thickness less than about 1 mil. Low density polyethylene and relatively soft polypropylene are particularly preferred. The polymeric film can also be a coextruded film including, for example, an adhesive polymer such as ethylene methyl acrylate copolymer in the layer adjacent the nonwoven material and a polyolefin such as low density polyethylene or polypropylene in the outer layer. The adhesive layer preferably is about 20% by weight of the coextruded film and the outer layer preferably is about 80% by weight of the coextruded film.

According to another embodiment of the present invention, a first web of extruded multicomponent polymeric strands made as described above is bonded to a second web of extruded polymeric strands, the first and second webs being positioned in laminar surface-to-surface relationship. The second web may be a spunbond material, but for applications such as garment material for medical apparel, the second layer can be made by well known meltblowing techniques. The meltblown layer can act as a liquid barrier. Such meltblowing techniques can be made in accordance with U.S. Pat. No. 4,041,203 of the disclosure of which is incorporated herein by reference. U.S. Pat. No. 4,041,203 references the following publications on meltblowing techniques which are also incorporated herein by reference: An article entitled "Superfine Thermoplastic Fibers" appearing in INDUSTRIAL & ENGINEERING CHEMISTRY, Vol. 48, No. 8, pp. 1342-1346 which describes work done at the Naval Research Laboratories in Washington, D.C.; Naval Research Laboratory Report 111437, dated Apr. 15, 1954; U.S. Pat. Nos. 3,715,251; 3,704,198; 3,676,242; and 3,595,245; and British Specification No. 1,217,892.

The meltblown layer can comprise substantially the same composition as the second component B of the multicomponent strands in the first web. The two webs are thermal point bonded together to form a cloth-like material. When the first and second webs are bonded together and the ethylene alkyl acrylate copolymer is present in both the second component B of the multicomponent strands in the first web and the second web, the bonds between the webs are more durable and the composite material has increased abrasion resistance.

Figure 4:
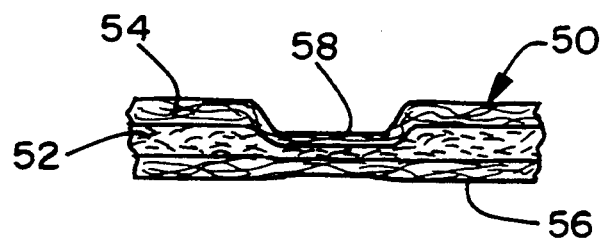
FIG. 4 is a cross-sectional view of the multilayer fabric of FIG. 3.

A third layer of nonwoven fabric comprising multicomponent polymeric strands, as in the first web, can be bonded to the side of the second web opposite from the first web. When the second web is a meltblown layer, the meltblown layer is sandwiched between two layers of multicomponent material. Such material 50 is illustrated in FIGS. 3 and 4 and is advantageous as a medical garment material because it contains a liquid penetration resistant middle layer 52 with relatively soft layers of fabric 54 and 56 on each side for better softness and feel. The material 50 is preferably thermal point bonded. When thermal point bonded, the individual layers 52, 54, and 56 are fused together at bond points 58.

Such composite materials may be formed separately and then bonded together or may be formed in a continuous process wherein one web is formed on top of the other. Both of such processes are well known to those skilled in the art and are not discussed here in further detail. U.S. Pat. No. 4,041,203, which is incorporated herein by reference above, discloses a continuous process for making such composite materials.

The following Examples 1-9 are designed to illustrate particular embodiments of the present invention and to teach one of ordinary skill in the art in the manner of carrying out the present invention. Comparative Examples 1 and 2 are designed to illustrate the advantages of the present invention. It should be understood by those skilled in the art that the parameters of the present invention will vary somewhat from those provided in the following Examples depending on the particular processing equipment that is used and the ambient conditions.

COMPARATIVE EXAMPLE 1

A nonwoven fabric web comprising continuous bicomponent filaments was made with the process illustrated in FIG. 1 and described above. The configuration of the filaments was side-by-side, the weight ratio of one side to the other side being 1:1. The spinhole geometry was 0.6 mm D with an L/D ratio of 4:1 and the spinneret had 645 openings arranged with 50 openings per inch in the machine direction. The composition of component A was 100% by weight PD-3445 polypropylene from Exxon of Houston, Tex., and the composition of component B was 100% by weight ASPUN 6811A linear low density polyethylene from Dow Chemical Company of Midland, Mich. The melt temperature in the spin pack was 450° F. and the spinhole throughput was 0.5 GHM. The quench air flow rate was 15 scfm and the quench air temperature was 53° F. The aspirator feed temperature was 350° F. and the manifold pressure was 4.2 psi. The resulting web was thermal point bonded at pattern/anvil bond temperatures of 242°/243° F. The bond pattern had regularly spaced bond areas with 250 bond points per square inch and a total bond area of 15%.

EXAMPLE 1

A nonwoven fabric web comprising continuous bicomponent filaments was made with the process illustrated in FIG. 1 and described above. The configuration of the filaments was side-by-side, the weight ratio of one side to the other side being 1:1. The spinhole geometry was 0.6 mm D with an L/D ratio of 4:1 and the spinneret had 645 openings arranged with 50 openings per inch in the machine direction. The composition of component A was 100% by weight PD-3445 polypropylene from Exxon of Houston, Tex., and the composition of component B was 95% by weight ASPUN 6811A polyethylene from Dow Chemical Company of Midland, Mich. and 5% by weight ENATHENE 720-009 ethylene n-butyl acrylate from Quantum. The melt temperature in the spin pack was 432° F. and the spinhole throughput was 0.7 GHM. The quench air flow rate was 16 scfm and the quench air temperature was 53° F. The aspirator feed temperature was 368° F. and the manifold pressure was 3.8 psi. The resulting web was thermal point bonded at pattern/anvil bond temperatures of 244°/246° F. The bond pattern had regularly spaced bond areas with 250 bond points per square inch and a total bond area of 15%.

EXAMPLE 2

A nonwoven fabric web comprising continuous bicomponent filaments was made with the process illustrated in FIG. 1 and described above. The configuration of the filaments was side-by-side, the weight ratio of one side to the other side being 1:1. The spinhole geometry was 0.6 mm D with an L/D ratio of 4:1 and the spinneret had 645 openings arranged with 50 openings per inch in the machine direction. The composition of component A was 100% by weight PD-3445 polypropylene from Exxon of Houston, Texas, and the composition of component B was 90% by weight ASPUN 6811A polyethylene from Dow Chemical Company of Midland, Mich. and 10% by weight ENATHENE 720-009 ethylene n-butyl acrylate from Quantum. The melt temperature in the spin pack was 431° F. and the spinhole throughput was 0.7 GHM. The quench air flow rate was 15 scfm and the quench air temperature was 53° F. The aspirator feed temperature was 359° F. and the manifold pressure was 3.8 psi. The resulting web was thermal point bonded at pattern/anvil bond temperatures of 243°/247° F. The bond pattern had regularly spaced bond areas with 250 bond points per square inch and a total bond area of 15%.

EXAMPLE 3

A nonwoven fabric web comprising continuous bicomponent filaments was made with the process illustrated in FIG. 1 and described above. The configuration of the filaments was side-by-side, the weight ratio of one side to the other side being 1:1. The spinhole geometry was 0.6 mm D with an L/D ratio of 4:1 and the spinneret had 645 openings arranged with 50 openings per inch in the machine direction. The composition of component A was 100% by weight PD-3445 polypropylene from Exxon of Houston, Tex., and the composition of component B was 85% by weight ASPUN 6811A polyethylene from Dow Chemical Company of Midland, Mich. and 15% by weight ENATHENE 720-009 ethylene n-butyl acrylate from Quantum. The melt temperature in the spin pack was 431° F. and the spinhole throughput was 0.7 GHM. The quench air flow rate was 15 scfm and the quench air temperature was 53° F. The aspirator feed temperature was 359° F. and the manifold pressure was 3.8 psi. The resulting web was thermal point bonded at pattern/anvil bond temperatures of 243°/247° F. The bond pattern had regularly spaced bond areas with 250 bond points per square inch and a total bond area of 15%.

Fabric samples from Comparative Example 1 and Examples 1-3 were tested to determine their physical properties. The data from these tests are shown in Table 1. The grab tensile was measured according to ASTM D 1682, and the drape stiffness was measured according to ASTM D 1388.

The trapezoid tear is a measurement of the tearing strength of fabrics when a constantly increasing load is applied parallel to the length of the specimen. The trapezoid tear was measured according to ASTM D 1117-14 except that the tearing load was calculated as the average of the first and highest peaks recorded rather than of the lowest and highest peaks.

The abrasion resistance was measured by the double head rotary platform (Tabor) test. The Tabor test was performed according to ASTM D-1175 using a 125 gram rubber wheel. The abrasion resistance was measured in cycles to photo.

The cup crush test evaluates fabric stiffness by measuring the peak load required for a 4.5 cm diameter hemispherically shaped foot to crush a 9"×9" piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which might affect the peak load. The peak load is measured while the foot descends at a rate of about 0.25 inches per second (15 inches per minute) utilizing a Model FTD-G-500 load cell (500 gram range) available from the Schaevitz Company, Tennsauken, N.J.

TABLE 1

| Property | COMPARATIVE EXAMPLE 1 | EXAMPLE 1 | EXAMPLE 2 | EXAMPLE 3 |
| --- | --- | --- | --- | --- |
| Actual Basis Weight (osy) | 1.34 | 1.43 | 1.29 | 1.38 |
| Caliper (in) | 0.016 | 0.014 | 0.021 | 0.018 |
| Denier (dpF) | 2.3 | 2.8 | 2.8 | 2.8 |
| Grab Tensile | | | | |
| MD Peak Load (lb) | 5.54 | 7.3 | 7.5 | 8.4 |
| MD % Strain | 57 | 90.04 | 144.3 | 132.4 |
| MD Peak Energy (in-lb) | 6.3 | 13.0 | 20.1 | 19.12 |
| CD Peak Load (lb) | 5.50 | 6.5 | 5.2 | 5.1 |
| CD % Strain | 100 | 153.1 | 262.3 | 251.4 |
| CD Peak Energy (in-lb) | 11.0 | 18.2 | 19.3 | 21.8 |
| Cup Crush Peak Load (g) | 40 | 27 | 10 | 13 |
| Energy (g-mm) | 736 | 417 | 115 | 180 |
| Tabor Abrasion Resistance (cycles) | | | | |
| Face | 5 | 12 | 90+ | 58 |
| Anvil | 5 | 9 | 53 | 24 |
| Drape Stiffness (cm) | | | | |
| MD | — | 1.98 | 1.8 | 1.6 |
| CD | — | 1.59 | 1.29 | 1.39 |

As can be seen from the data in Table 1, the abrasion resistance of samples from Examples 1-3 was significantly greater than the abrasion resistance of the sample from Comparative Example 1. This demonstrates the effect of the addition of ethylene butyl acrylate copolymer to the second component of multicomponent filaments which are formed into a single layer web In addition, Table 1 demonstrates that the addition of ethylene butyl acrylate increases the strength of the fabric as shown by the measuring peak load in the machine direction, increases the toughness of the fabric as shown by the increasing % strain and peak energy values, increases the softness and conformability of the fabric as shown by the decreasing cup crush load and energy values, and increases the bulk of the fabric as shown by the increasing caliper.

COMPARATIVE EXAMPLE 2

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight PD-3445 polypropylene from Exxon of Houston, Tex., and the sheath composition was 100% by weight ASPUN 6811A linear low density polyethylene from Dow Chemical Company of Midland, Mich. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The web was thermal point bonded to opposite sides of a middle meltblown nonwoven fabric web comprising 100% by weight ASPUN 6811A polyethylene. The meltblown web was made in accordance with U.S. Pat. No. 4,041,203. The resulting composite was thermal point bonded at a bond temperature of 260° F. The bond pattern had regularly spaced bond areas with 270 bond points per square inch and a total bond area of about 18%.

EXAMPLE 4

A first nonwoven fabric web comprising continuous bicomponent filaments was made with the process illustrated in FIG. 1 and described above. The configuration of the filaments was concentric sheath/core, the weight ratio of sheath to core being 1:1. The spinhole geometry was 0.6 mm D with an L/D ratio of 4:1 and the spinneret had 525 openings arranged with 50 openings per inch in the machine direction. The core composition was 100% by weight 3445 polypropylene from Exxon of Houston, Tex., and the sheath composition was 85% by weight ASPUN 6811A polyethylene from Dow Chemical Company of Midland, Mich. and 15% by weight ENATHENE 720-009 ethylene n-butyl acrylate from Quantum Chemical Corporation, USI Division of Cincinnati, Ohio. The melt temperature in the spin pack was 430° F. and the spinhole throughput was 0.7 GHM. The quench air flow rate was 22 scfm and the quench air temperature was 55° F. The aspirator feed temperature was 55° F. and the manifold pressure was 5 psi. The first web was thermal point bonded to opposite sides of a middle meltblown nonwoven fabric web comprising 100% by weight ASPUN 6811A polyethylene. The meltblown web was made in accordance with U.S. Pat. No. 4,041,203. The resulting composite was thermal point bonded at a bond temperature of 260° F. The bond pattern had regularly spaced bond areas with 270 bond points per square inch and a total bond area of about 18%.

EXAMPLE 5

A composite nonwoven fabric was made according to the process described in Example 4 except that the meltblown layer comprised 100% by weight 3495G polypropylene from Exxon.

EXAMPLE 6

A composite nonwoven fabric was made according to the process described in Example 4 except that the sheath of the filaments in the spunbond layers comprised 85% by weight 25355 high density polyethylene from Dow Chemical Company and 15% by weight of ENATHENE 720-009 ethylene n-butyl acrylate copolymer from Quantum.

EXAMPLE 7

A composite nonwoven fabric was made according to the process described in Example 4 except that the sheath of the filaments in the spunbond layers comprised 85% by weight 25355 high density polyethylene from Dow Chemical Company and 15% by weight of ENATHENE 720-009 ethylene n-butyl acrylate copolymer from Quantum and the meltblown layer comprised 100% by weight 3495G polypropylene from Exxon.

EXAMPLE 8

A composite nonwoven fabric was made according to the process described in Example 4 except that the sheath of the filaments in the spunbond layers comprised 85% by weight ASPUN 6808A polyethylene from Dow Chemical Company and 15% by weight of ENATHENE 720-009 ethylene n-butyl acrylate copolymer from Quantum.

EXAMPLE 9

A composite nonwoven fabric was made according to the process described in Example 4 except that the sheath of the filaments in the spunbond layers comprised 85% by weight ASPUN 6808A polyethylene from Dow Chemical Company and 15% by weight of ENATHENE 720-009 ethylene n-butyl acrylate copolymer from Quantum and the meltblown layer comprised 100% by weight 3495G polypropylene from Exxon.

The Martindale Abrasion test used for Comparative Example 2 and Examples 4–9 measures the resistance to the formation of pills and other related surface changes on textile fabrics under light pressure using a Martindale tester. The Martindale Abrasion was measured according to ASTM 04970-89 except that the value obtained was the number of cycles required by the Martindale tester to create a 0.5 inch hold in the fabric sample.

TABLE 2

| PROPERTY | COMPARATIVE EXAMPLE 2 | EXAMPLE 4 | EXAMPLE 5 | EXAMPLE 6 | EXAMPLE 7 | EXAMPLE 8 | EXAMPLE 9 |
| --- | --- | --- | --- | --- | --- | --- | --- |
| ACTUAL BASIS WEIGHT | 1.60 | 1.71 | 1.63 | 1.75 | 1.54 | 1.70 | 1.56 |
| GRAB TENSILE | | | | | | | |
| MD/CD Average Peak Energy (in-lb) | 32.00 | 36.03 | 22.62 | 36.07 | 18.21 | 36.22 | 25.61 |

TABLE 2-continued

| PROPERTY | COMPARATIVE EXAMPLE 2 | EXAMPLE 4 | EXAMPLE 5 | EXAMPLE 6 | EXAMPLE 7 | EXAMPLE 8 | EXAMPLE 9 |
|---|---|---|---|---|---|---|---|
| MD/CD Average Peak Load (lb) | 9.77 | 14.12 | 10.31 | 11.73 | 6.99 | 14.51 | 11.14 |
| MD Trapezoid Tear (lb) | 6.75 | 11.36 | 10.64 | 14.09 | 10.70 | 14.77 | 12.42 |
| CD Trapezoid Tear (lb) | 4.10 | 6.99 | 4.90 | 4.78 | 2.55 | 5.88 | 4.18 |
| Martindale Abrasion (cycles/0.5 in. hole) | 175 | 524 | 592 | 291 | 222 | 885 | 826 |
| Mullen Burst (psi) | 13.0 | 21.1 | — | 20.7 | 19.7 | 21.9 | 21.8 |
| MD Drape Stiffness (in) | 2.34 | 3.15 | 4.03 | 2.40 | 3.47 | 2.52 | 3.31 |
| CD Drape Stiffness (in) | 1.72 | 1.74 | 1.85 | 1.51 | 1.61 | 1.66 | 1.41 |
| Cup Crush/Peak Load (g) | 59 | 95 | 118 | 77 | 97 | 71 | 102 |
| Cup Crush/ Total Energy (g/mm) | 1093 | 1690 | 2410 | 1395 | 1731 | 1328 | 1925 |

As can be seen from the data in Table 2, the abrasion resistance of samples from Examples 4–9 was significantly greater than the abrasion resistance of Comparative Example 2. This demonstrates the effect of the addition of the ethylene butyl acrylate copolymer to the second component of the multicomponent filaments. The strength and softness properties of the samples from Examples 4–9 varied depending on the polyolefins in the spunbond and meltblown layers. Directly comparing Comparative Example 2 to Example 4, it can be seen that the addition of the ethylene butyl acrylate copolymer increased the strength properties of the composite fabric. However, unlike the addition of ethylene butyl acrylate to multicomponent filaments forming a single layer web, the softness properties were not improved.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

We claim:

1. A nonwoven fabric comprising extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a blend of a polyolefin and ethylene alkyl acrylate copolymer.

2. A nonwoven fabric as in claim 1 wherein the ethylene alkyl acrylate copolymer is present in an amount from about 2 to about 50% by weight of the second component and the polyolefin is present in an amount from about 98 to about 50% by weight of the second component.

3. A nonwoven fabric as in claim 1 wherein the ethylene alkyl acrylate copolymer is present in an amount from about 5 to about 25% by weight of the second component and the polyolefin is present in an amount from about 95 to about 75% by weight of the second component.

4. A nonwoven fabric as in claim 1 wherein the ethylene alkyl acrylate copolymer is present in an amount from about 10 to about 20% by weight of the second component and the polyolefin is present in an amount from about 90 to about 80% by weight of the second component.

5. A nonwoven fabric as in claim 1 wherein the first polymeric component is present in an amount from about 20 to about 80% by weight of the strands and the second polymeric component is present in an amount from about 80 to about 20% by weight of the strands.

6. A nonwoven fabric as in claim 1 wherein the first polymeric component is present in an amount from about 40 to about 60% by weight of the strands and the second polymeric component is present in an amount from about 60 to about 40% by weight of the strands.

7. A nonwoven fabric as in claim 1 wherein the strands are continuous filaments.

8. A nonwoven fabric as in claim 1 wherein the ethylene alkyl acrylate copolymer is selected from the group consisting of ethylene butyl acrylate copolymer, ethylene ethyl acrylate copolymer, and ethylene methyl acrylate copolymer.

9. A nonwoven fabric as in claim 1 wherein the polyolefin of the second component is selected from the group consisting of polyethylene, polypropylene, and copolymers of ethylene and propylene.

10. A nonwoven fabric as in claim 1 wherein the polyolefin of the second component comprises linear low density polyethylene.

11. A nonwoven fabric as in claim 1 wherein the first component has a first melting point and the second component has a second melting point less than the first melting point.

12. A nonwoven fabric as in claim 1 wherein the first component has a first melting point and the second component has a second melting point less than the first melting point, the second component comprising polyethylene.

13. A nonwoven fabric as in claim 1 wherein the first component has a first melting point and the second component has a second melting point less than the first melting point, the second component comprising linear low density polyethylene.

14. A nonwoven fabric as in claim 1 wherein the first component has a first melting point and the second component has a second melting point less than the first melting point, the first component comprising a polyolefin.

15. A nonwoven fabric as in claim 1 wherein the first component has a first melting point and the second component has a second melting point less than the first melting point, the first component being selected from the group consisting of polypropylene and copolymers of propylene and ethylene, and the second component comprising polyethylene.

16. A nonwoven fabric as in claim 1 wherein the first component has a first melting point and the second component has a second melting point less than the first melting point, the first component being selected from the group consisting of polypropylene and copolymers of propylene and ethylene, and the second component comprising linear low density polyethylene.

17. A nonwoven fabric as in claim 1 wherein the first component has a first melting point and the second component has a second melting point less than the first melting point, the first component comprising polypropylene and the second component comprising random copolymers of propylene and ethylene.

18. A nonwoven fabric as in claim 1 wherein :
the first polymeric component is present in an amount from about 20 to about 80% by weight of the strands and the second polymeric component is present in an amount from about 80 to about 20% by weight of the strands; and
the ethylene alkyl acrylate copolymer is present in an amount from about 2 to about 50% by weight of the second component and the polyolefin is present in an amount from about 98 to about 50% by weight of the second component.

19. A nonwoven fabric as in claim 18 wherein the first component comprises polypropylene and the second component comprises polyethylene.

20. A nonwoven fabric as in claim 18 wherein the first component comprises polypropylene and the second component comprises linear low density polyethylene.

21. A nonwoven fabric as in claim 1 wherein :
the first polymeric component is present in an amount from about 20 to about 80% by weight of the strands and the second polymeric component is present in an amount from about 80 to about 20% by weight of the strands; and
the ethylene alkyl acrylate copolymer is present in an amount from about 5 to about 25% by weight of the second component and the polyolefin is present in an amount from about 95 to about 75% by weight of the second component 22. A nonwoven fabric as in claim 21 wherein the first component comprises polypropylene and the second component comprises polyethylene.

23. A nonwoven fabric as in claim 21 wherein the first component comprises polypropylene and the second component comprises linear low density polyethylene.

24. A nonwoven fabric as in claim 1 wherein :
the first polymeric component is present in an amount from about 20 to about 80% by weight of the strands and the second polymeric component is present in an amount from about 80 to about 20% by weight of the strands; and
the ethylene alkyl acrylate copolymer is present in an amount from about 10 to about 20% by weight of the second component and the polyolefin is present in an amount from about 90 to about 80% by weight of the second component.

25. A nonwoven fabric as in claim 24 wherein the first component comprises polypropylene and the second component comprises polyethylene.

26. A nonwoven fabric as in claim 24 wherein the first component comprises polypropylene and the second component comprises linear low density polyethylene.

27. A nonwoven fabric as in claim 1, wherein the strands form a web and further comprising a layer of polymer film bonded to the web.

28. A nonwoven fabric comprising continuous multicomponent polymeric filaments including from about 20 to about 80% by weight of a first polymeric component and from about 80 to about 20% by weight of a second polymeric component, the multicomponent filaments having a cross-section, a length, and a peripheral surface, the first and second components being arranged in substantially distinct zones across the cross-section of the multicomponent filaments and extending continuously along the length of the multicomponent filaments, the second component constituting at least a portion of the peripheral surface of the multicomponent filaments continuously along the length of the multicomponent filaments and including a blend of from about 98 to about 50% by weight of a polyolefin and from about 2 to about 50% by weight of ethylene alkyl acrylate copolymer.

29. A nonwoven fabric as in claim 28 wherein the first component comprises polypropylene and the second component comprises polyethylene.

30. A nonwoven fabric as in claim 28 wherein the first component comprises polypropylene and the second component comprises linear low density polyethylene.

31. A nonwoven fabric as in claim 28 wherein the ethylene alkyl acrylate copolymer is selected from the group consisting of ethylene butyl acrylate copolymer, ethylene ethyl acrylate copolymer, and ethylene methyl acrylate copolymer.

32. A nonwoven fabric as in claim 28 wherein the filaments form a web and further comprising a layer of polymeric film bonded to the web.

33. A nonwoven fabric comprising:
a first web of extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a first blend of a polyolefin and an ethylene alkyl acrylate copolymer; and
a second web of extruded polymeric strands composed of but a single polymeric component comprising a second blend of a polyolefin and ethylene alkyl acrylate copolymer, the first and second webs being positioned in laminar surface-to-surface relationship and bonded together to form an integrated fabric.

34. A nonwoven fabric as in claim 33 wherein the strands of the second web are meltblown.

35. A nonwoven fabric as in claim 33 comprising a third web of extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a third blend of a polyolefin and ethylene alkyl acrylate copolymer, the first web being bonded to one side of the second web and the third web being bonded to an opposite side of the second web.

36. A nonwoven fabric as in claim 35 wherein the strands of the second web are meltblown.

37. A nonwoven fabric as in claim 33 wherein the ethylene alkyl acrylate copolymer is present in the first and second blends in an amount from about 2 to about 50% by weight and the polyolefin is present in the first and second blends in an amount from about 98 to about 50% by weight.

38. A nonwoven fabric as in claim 33 wherein the ethylene alkyl acrylate copolymer is present in the first and second blends in an amount from about 5 to about 25% by weight and the polyolefin is present in the first and second blends in an amount from about 95 to about 75% by weight.

39. A nonwoven fabric as in claim 33 wherein the ethylene alkyl acrylate copolymer is present in the first and second blends in an amount from about 10 to about 20% by weight and the polyolefin is present in the first and second blends in an amount from about 90 to about 80% by weight.

40. A nonwoven fabric as in claim 33 wherein the strands of the first web are continuous filaments.

41. A nonwoven fabric as in claim 33 wherein the ethylene alkyl acrylate copolymer is selected from the group consisting of ethylene butyl acrylate copolymer, ethylene ethyl acrylate copolymer, and ethylene methyl acrylate copolymer.

42. A nonwoven fabric as in claim 33 wherein the polyolefin of the second component of the first web and the polyolefin of the second web are selected from the group consisting of polyethylene, polypropylene, and copolymers of ethylene and propylene.

43. A nonwoven fabric as in claim 33 wherein the polyolefin of the second component of the first web and the polyolefin of the second web comprise linear low density polyethylene.

44. A nonwoven fabric as in claim 33 wherein the first component has a first melting point and the second component has a second melting point less than the first melting point.

45. A nonwoven fabric as in claim 33 wherein the first component has a first melting point and the second component has a second melting point less than the first melting point, the second component comprising polyethylene.

46. A nonwoven fabric as in claim 33 wherein the first component has a first melting point and the second component has a second melting point less than the first melting point, the second component comprising linear low density polyethylene.

47. A nonwoven fabric as in claim 33 wherein the first component has a first melting point and the second component has a second melting point less than the first melting point, the first component comprising a polyolefin.

48. A nonwoven fabric as in claim 33 wherein the first component has a first melting point and the second component has a second melting point less than the first melting point, the first component being selected from the group consisting of polypropylene and copolymers of propylene and ethylene, and the second component comprising polyethylene.

49. A nonwoven fabric as in claim 33 wherein the first component has a first melting point and the second component has a second melting point less than the first melting point, the first component being selected from the group consisting of polypropylene and copolymers of propylene and ethylene, and the second component comprising linear low density polyethylene.

50. A nonwoven fabric as in claim 33 wherein the first component has a first melting point and the second component has a second melting point less than the first melting point, the first component comprising polypropylene and the second component comprising random copolymers of propylene and ethylene.

51. A nonwoven fabric as in claim 33 wherein:
the first polymeric component is present in an amount from about 20 to about 80% by weight of the strands and the second polymeric component is present in an amount from about 80 to about 20% by weight of the strands; and
the ethylene alkyl acrylate copolymer is present in an amount from about 2 to about 50% by weight of the second component and the polyolefin is present in an amount from about 98 to about 50% by weight of the second component.

52. A nonwoven fabric as in claim 51 wherein the first component comprises polypropylene and the second component comprises polyethylene.

53. A nonwoven fabric as in claim 51 wherein the first component comprises polypropylene and the second component comprises linear low density polyethylene.

54. A nonwoven fabric as in claim 33 wherein:
the first polymeric component is present in an amount from about 20 to about 80% by weight of the strands and the second polymeric component is present in an amount from about 80 to about 20% by weight of the strands; and
the ethylene alkyl acrylate copolymer is present in an amount from about 5 to about 25% by weight of the second component and the polyolefin is present in an amount from about 95 to about 75% by weight of the second component.

55. A nonwoven fabric as in claim 52 wherein the first component comprises polypropylene and the second component comprises polyethylene.

56. A nonwoven fabric as in claim 54 wherein the first component comprises polypropylene and the second component comprises linear low density polyethylene.

57. A nonwoven fabric as in claim 33 wherein: the first polymeric component is present in an amount from about 20 to about 80% by weight of the strands and the second polymeric component is present in an amount from about 80 to about 20% by weight of the strands; and
the ethylene alkyl acrylate copolymer is present in an amount from about 10 to about 20% by weight of the second component and the polyolefin is present in an amount from about 90 to about 80% by weight of the second component.

58. A nonwoven fabric as in claim 57 wherein the first component comprises polypropylene and the second component comprises polyethylene.

59. A nonwoven fabric as in claim 57 wherein the first component comprises polypropylene and the second component comprises linear low density polyethylene.

60. A nonwoven fabric web comprising:

a first web of continuous multicomponent polymeric filaments including first and second polymeric components, the multicomponent filaments having a cross-section, a length, and a peripheral surface, the first and second components being arranged in substantially distinct zones across the cross-section of the multicomponent filaments and extending continuously along the length of the multicomponent filaments, the second component constituting at least a portion of the peripheral surface of the multicomponent filaments continuously along the length of the multicomponent filaments and including a first blend of a polyolefin and an ethylene alkyl acrylate copolymer; and a second web of extruded polymeric strands composed of but a single polymeric component comprising a second blend of a polyolefin and a ethylene alkyl acrylate copolymer; and a third web of continuous multicomponent polymeric filaments including first and second polymeric components, the multicomponent filaments having a cross-section, a length, and a peripheral surface, the first and second components being arranged in substantially distinct zones across the cross-section of the multicomponent filaments and extending continuously along the length of the multicomponent filaments, the second component constituting at least a portion of the peripheral surface of the multicomponent filaments continuously along the length of the multicomponent filaments and including a third blend of a polyolefin and ethylene alkyl acrylate copolymer, the first, second, and third webs being positioned in laminar surface-to-surface relationship, the first web being bonded to one side of the second web and the third web being bonded to an opposite side of the second web to form an integrated fabric.

61. A nonwoven fabric as in claim 60 wherein the strands of the second web are meltblown.

62. A nonwoven fabric as in claim 60 wherein:

the first polymeric component is present in an amount from about 20 to about 80% by weight of the filaments and the second polymeric component is present in an amount from about 80 to about 20% by weight of the filaments; and the ethylene alkyl acrylate copolymer is present in the second component of the first and third webs and in the single component of the second web in an amount from about 2 to about 50% by weight and the polyolefin is present in the second component of the first and third webs and the single component of the second web in an amount from about 98 to about 50% by weight.

63. A nonwoven fabric as in claim 60 wherein the ethylene alkyl acrylate copolymer is selected from the group consisting of ethylene butyl acrylate copolymer, ethylene ethyl acrylate copolymer, and ethylene methyl acrylate copolymer.

64. A nonwoven fabric as in claim 63 wherein the first component of the first and third webs comprises polypropylene and the second component of the first and third webs and the single component of the second web comprises polyethylene.

65. A nonwoven fabric as in claim 63 wherein the first component of the first and third webs comprises polypropylene and the second component of the first and third webs and the single component of the second web comprises linear low density polyethylene.

66. A nonwoven fabric comprising:

a first web of extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a first blend of a polyolefin and ethylene alkyl acrylate copolymer; and a second web of extruded polymeric strands, the first and second webs being positioned in laminar surface-to-surface relationship and bonded together to form an integrated fabric.

67. A nonwoven fabric as in claim 66 wherein the ethylene alkyl acrylate copolymer is selected from the group consisting of ethylene butyl acrylate copolymer, ethylene ethyl acrylate copolymer, and ethylene methyl acrylate copolymer.

68. A personal care article comprising a layer of nonwoven fabric comprising extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a blend of a polyolefin and ethylene alkyl acrylate copolymer.

69. A personal care article as in claim 68 wherein the ethylene alkyl acrylate copolymer is selected from the group consisting of ethylene butyl acrylate copolymer, ethylene ethyl acrylate copolymer, and ethylene methyl acrylate copolymer.

70. A personal care article as in claim 68, wherein the strands form a web and further comprising a layer of polymer film bonded to the web.

71. A garment comprising a layer of nonwoven fabric comprising:

a first web of extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a first blend of a polyolefin and an ethylene alkyl acrylate copolymer; and a second web of extruded polymeric strands composed of but a single polymeric component comprising a second blend of a polyolefin and ethylene alkyl acrylate copolymer, the first and second webs being positioned in laminar surface-to-surface relationship and bonded together to form an integrated fabric.

72. A garment as in claim 71 wherein the strands of the second web are meltblown.

73. A garment as in claim 71 wherein the layer of nonwoven fabric comprises a third web of extruded multicomponent polymeric strands including first and second polymeric components, the multicomponent strands having a cross-section, a length, and a peripheral surface, the first and second components being arranged in substantially distinct zones across the cross-section of the multicomponent strands and extending continuously along the length of the multicomponent strands, the second component constituting at least a portion of the peripheral surface of the multicomponent strands continuously along the length of the multicomponent strands and including a third blend of a polyolefin and ethylene alkyl acrylate copolymer, the first web being bonded to one side of the second web and the third web being bonded to an opposite side of the second web.

74. A garment as in claim 73 wherein the strands of the second web are meltblown.

75. A garment as in claim 71 wherein the ethylene alkyl acrylate copolymer is selected from the group consisting of ethylene butyl acrylate copolymer, ethylene ethyl acrylate copolymer, and ethylene methyl acrylate copolymer.

* * * * *